United States Patent
Isaka et al.

(10) Patent No.: US 7,442,539 B2
(45) Date of Patent: Oct. 28, 2008

(54) METHOD AND EQUIPMENT FOR CULTIVATING ANAEROBIC AMMONIUM-OXIDIZING BACTERIA

(75) Inventors: Kazuichi Isaka, Tokyo (JP); Tatsuo Sumino, Tokyo (JP); Satoshi Tsuneda, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 333 days.

(21) Appl. No.: 11/373,271

(22) Filed: Mar. 13, 2006

(65) Prior Publication Data

US 2006/0205055 A1    Sep. 14, 2006

(30) Foreign Application Priority Data

Mar. 14, 2005 (JP) ............................. 2005-071558
Mar. 15, 2005 (JP) ............................. 2005-073398
Feb. 14, 2006 (JP) ............................. 2006-037163

(51) Int. Cl.
*C12N 1/20*    (2006.01)

(52) U.S. Cl. .................................................. 435/252.1
(58) Field of Classification Search ............... 435/252.1
See application file for complete search history.

(56) References Cited

FOREIGN PATENT DOCUMENTS

JP    A-09-187272    7/1997
JP    A-2001-037467    2/2001

OTHER PUBLICATIONS

Isaka Kazuichi et al., "Growth characteristic of anaerobic ammonium-oxidizing bacteria in an anaerobic biological filtrated reactor", Applied Microbiology and Biotechnology, vol. 70, No. 1, Mar. 2006, pp. 47-52.

Khin et al., "Novel microbial nitrogen removal processes", Biotechnology Advances, Elsevier Publishing Barking, GB, vol. 22, No. 7, Sep. 2004, pp. 519-532.

Strous M. et al., "The sequencing batch reactor as a powerful tool for the study of slowly growing anaerobic ammonium-oxidizing microorganisms", Applied Microbiology and Biotechnology, Springer Verlag, Berlin, DE, vol. 50, No. 5, Nov. 1998, pp. 589-596.

Stous M. et al., "Missing lithotroph identified as new planctomycete", Nature, London, vol. 400, No. 6743, Jul. 29, 1999, pp. 446-449.

Strous, M. et al., "The sequencing batch reactor as a powerful tool for the study of slowing growing anaerobic ammonium-oxidizing microorganisms", Appl Microbiology Biotechnology, 50; pp. 589-596, Kluyver Laboratory for Biotechnology, Delft University of Technology, Delft, The Netherlands, 1998.

Strous, Marc et al., "Missing lithotroph identified as new planctomycete", Nature, vol. 400 Jul. 29, 1999.

*Primary Examiner*—Tekchand Saidha
(74) *Attorney, Agent, or Firm*—Oliff & Berridge, PLC

(57) ABSTRACT

The present invention can feed substrates without waste to generate seed sludge with high bacterial cell concentrations and can start up operation within a short time, in cultivating anaerobic ammonium oxidizing bacteria with ammonium and nitrite as substrates. Equipment for cultivating anaerobic ammonium-oxidizing bacteria, which cultivates, in a cultivation tank, novel anaerobic ammonium-oxidizing bacteria that anaerobically denitrify nitrite and ammonium used as substrates, comprises an ammonium feed device which feeds ammonium at a given concentration into the cultivation tank, a nitrite feed device which feeds nitrite at a given concentration into the cultivation tank, and a control device which controls a feed rate Y of the substrate.

33 Claims, 6 Drawing Sheets

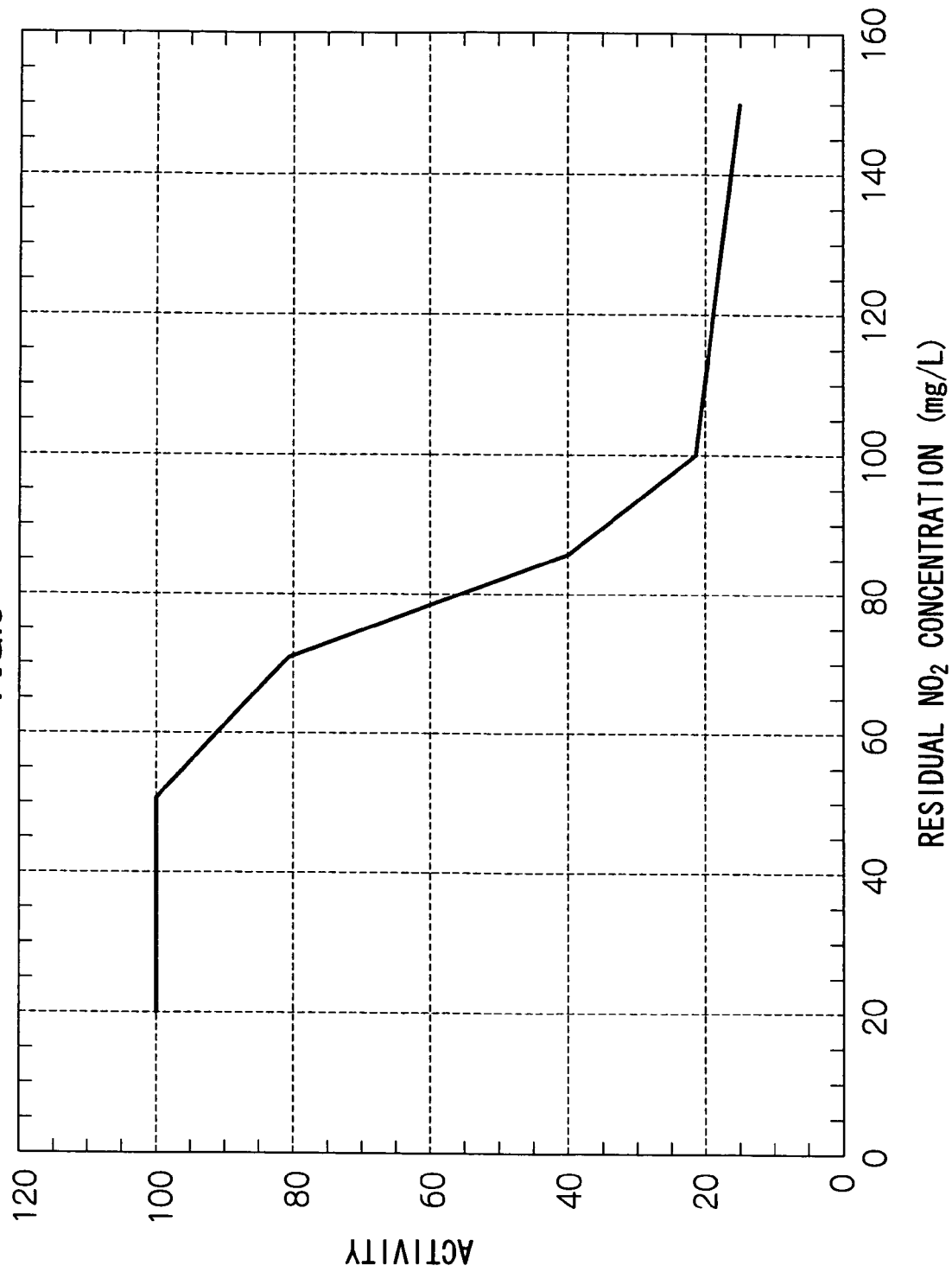

SEQUENCE LISTING

```
<160> NUMBER OF SEQ ID NOS: 9

<210> SEQ ID NO 1
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 1
tcgagaatct ttcgcaatgc ccgaaagggt gacgaagcga cgccgcgtgc gggaagaagg        60
ccttcgggtt gtaaaccgct gtcgggagtt aggaaatgca aggatgttaa tagcattctt      120
gcttgactaa ggctccggag gaagccacgg ctaactctgt gccagcagcc gcggtaatac      180
agaggcggca agcgttgttc ggaattattg ggcgtaaaga gcacgtaggc ggctgtgtaa      240
```

```
gtcggttgtg aaagccttcc gcttaacgga agaacggcat ccgatactgc atagcttgag    300
tgcgggaggg gagagtggaa cttctggtgg agcggtgaaa tgcgtagata tcagaaggaa    360
caccggcggc gaaggcgact ctctggtccg taactgacgc tgagtgtgcg aaagctaggg    420
gagcaaacgg gattagatac cccggtagtc ctagccgtaa acgatggg                 468
```

<210> SEQ ID NO 2
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 2

```
tcgagaatct ttcgcaatgc ccgcaagggt gacgaagcga cgccgcgtgc gggaagaagg     60
ccttcgggtt gtaaaccgct gtcgggagtt aggaagtgca aggatgttaa tagcgttctt    120
gcttgactaa ggctccggag gaagccacgg ctaactctgt gccagcagcc gcggtaatac    180
agaggcggca agcgttgttc ggaattattg ggcgtaaaga gcacgtaggc ggctgtgtaa    240
gtcggttgtg aaagccttcc gcttaacgga agaacggcat ccgatactgc atagcttgag    300
tgcgggaggg gagagtggaa cttctggtgg agcggtgaaa tgcgtagata tcagaaggaa    360
caccggcggc gaaggcgact ctctggtccg taactgacgc tgagtgtgcg aaagctaggg    420
gagcaaacgg gattagatac cccggtagtc ctagccgtaa acgatggg                 468
```

<210> SEQ ID NO 3
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction;
      DNA sequence of 16S rRNA gene

<400> SEQUENCE: 3

```
tcgagaatct ttcgcaatgc ccgaaagggt gacgaagcga cgccgcgtgc gggaagaagg     60
ccttcgggtt gtaaaccgct gtcgggagtt aggaagtgca aggatgttaa tagcgttctt    120
gcttgactaa ggctccggag gaagccacgg ctaactctgt gccagcagcc gcggtaatac    180
agaggcggca agcgttgttc ggaattattg ggcgtaaaga gcacgtaggc ggctgtgtaa    240
gtcggttgtg aaagccttcc gcttaacgga agaacggcat ccgatactgc atagcttgag    300
tgcgggaggg gagagtggaa cttctggtgg agcggtgaaa tgcgtagata tcagaaggaa    360
caccggcggc gaaggcgact ctctggtccg taactgacgc tgagtgtgcg aaagctaggg    420
gagcaaacgg gattagatac cccggtagtc ctagccgtaa acgatggg                 468
```

<210> SEQ ID NO 4
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 4

```
tcgagaatct ttcgcaatgc ccgaaagggt gacgaagcga cgccgcgtgt gggatgaagg     60
ccctcgggtt gtaaaccact gtcgggagtt aagaattgta ggggtgctaa tagtatttct    120
```

```
acttgactaa ggctccggag gaagccacgg ctaactctgt gccagcagcc gcggtaatac      180
agaggcggca agcgttgttc ggaattattg ggcgtaaaga gcatgtaggc ggctatgtaa      240
gtcggttgtg aaagccttcc gcttaacgga agaatggcgg tcgaaactgc atggcttgag      300
tgcgggaggg gagagtggaa cttctggtgg agcggtgaaa tgcgtagata tcagaaggaa      360
cgtcggcggc gaaagcgact ctctagaccg taactgacgc tgagtgtgcg aaagctaggg      420
gagcaaacgg gattagatac cccggtagtc ctagccgtaa acgatggg                   468

<210> SEQ ID NO 5
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 5
tcgagaatct ttcgcaatgc ccgcaagggt gacgaagcga cgccgcgtgc gggaagaagg      60
ccttcgggtt gtaaaccgct gtcgggagtt aggaagtgca aggatgttaa tagcgttctt     120
gcttgactaa ggctccggag gaagccacgg ctaactctgt gccagcagcc gcggtaatac     180
agaggcggca agcgttgttc ggaattattg ggcgtaaaga gcacgtaggc ggccgtgtaa     240
gtcggttgtg aaagccttcc gctcaacgga aggacggcat ccgatactgc atggctcgag     300
tgcgggaggg gagagtggaa cttctggtgg agcggtgaaa tgcgtagata tcagaaggaa     360
caccggcggc gaaggcgact ctctggtccg taactgacgc tgagtgtgcg aaagctaggg     420
gagcaaacgg gattagatac cccggtagtc ctagccgtaa acgatggg                   468

<210> SEQ ID NO 6
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 6
tcgagaatct ttcgcaatgc ccgaaagggt gacgaagcga cgccgcgtgc gggaagaagg      60
ccttcgggtt gtaaaccgct gtcgggagtt aagaagtgca gggatgttaa tagcgtctct     120
gcttgactaa ggctccggag gaagccacgg ctaactctgt gccagcagcc gcggtaatac     180
agaggcggca agcgttgttc ggaattattg ggcgtaaaga gcacgtaggc ggccgtgtaa     240
gtcggttgtg aaagccttcc gctcaacgga aggacggcat ccgatactgc atggctcgag     300
tgcgggaggg gagagtggaa cttctggtgg agcggtgaaa tgcgtagata tcagaaggaa     360
caccggcggc gaaggcgact ctctggtccg taactgacgc tgagtgtgcg aaagctaggg     420
gagcaaacgg gattagatac cccggtagtc ctagccgtaa acgatggg                   468

<210> SEQ ID NO 7
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene
```

```
<400> SEQUENCE: 7
tcgagaatct ttcgcaatgc ccgaaagggt gacgaagcga cgccgcgtgc gggaagaagg      60
ccttcgggtt gtaaaccgct gtcgggagtt aagaagtgcg gggatgttaa tagcgtcctt     120
gcttgactaa ggctccggag gaagccacgg ctaactctgt gccagcagcc gcggtaatac     180
agaggcggca agcgttgttc ggaattattg ggcgtaaaga gcacgtaggc ggccgcgtaa     240
gtcggttgtg aaagccttcc gctcaacgga aggacggcat ccgatactgc atggctcgag     300
tgcgggaggg gagagtggaa cttctggtgg agcggtgaaa tgcgtagata tcagaaggaa     360
caccggcggc gaaggcgact ctctggtccg taactgacgc tgagtgtgcg aaagctaggg     420
gagcaaacgg gattagatac cccagtagtc ctagccgtaa acgatggg                  468

<210> SEQ ID NO 8
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 8
tcgagaatct ttcgcaatgc ccgcaagggt gacgaagcga cgccgcgtgc gggaagaagg      60
ccttcgggtt gtaaaccgct gtcgggagtt aggaaatgca aggatgttaa tagcattctt     120
gcttgactaa ggctccggag gaagccacgg ctaactctgt gccagcagcc gcggtaatac     180
agaggcggca agcgttgttc ggaattattg ggcgtaaaga gcacgtaggc ggctgtgtaa     240
gtcggttgtg aaagccttcc gcttaacgga agaacggcat ccgatactgc atagcttgag     300
tgcgggaggg gagagtggaa cttctggtgg agcggtgaaa tgcgtagata tcagaaggaa     360
caccggcggc gaaggcgact ctctggtccg taactgacgc tgagtatgcg aaagctaggg     420
gagcaaacgg gattagatac cccggtagtc ctagccgtaa acgatggg                  468

<210> SEQ ID NO 9
<211> LENGTH: 468
<212> TYPE: DNA
<213> ORGANISM: unknown
<220> FEATURE:
<223> OTHER INFORMATION: microorganism belonging to genus planctomycetes
      responsible for anaerobic ammonium-oxidizing reaction; DNA
      sequence of 16S rRNA gene

<400> SEQUENCE: 9
tcgagaatct ttcgcaatgc ccgaaagggt gacgaagcga cgccgcgtgc gggaagaagg      60
ccttcgggtt gtaaaccgct gtcgggagtt aggaaatgca aggatgttaa tagcattctt     120
gcttgactaa ggctccggag gaagccacgg ctaactctgt gccagcagcc gcggtaatac     180
agaggcggca agcgttgttc ggaattattg ggcgtaaaga gcacgtaggc ggctgtgtaa     240
gtcggttgtg aaagccttcc gcttaacgga agaacggcat ccgatactgc atagcttgag     300
tgcgggaggg gagagtggaa cttctggtgg agcggtgaaa tgcgtagata tcagaaggaa     360
caccggcggc gaaagcgact ctctagaccg taactgacgc tgagtgtgcg aaagctaggg     420
gagcaaacgg gattagatac cccggtagtc ctagccgtaa acgatggg                  468
```

METHOD AND EQUIPMENT FOR CULTIVATING ANAEROBIC AMMONIUM-OXIDIZING BACTERIA

BACKGROUND OF THE INVENTION

1. Field of the Invention

The present invention relates to a method and equipment for cultivating anaerobic ammonium-oxidizing bacteria. Particularly, the present invention relates to a method and equipment for cultivating anaerobic ammonium-oxidizing bacteria, which are intended for efficiently cultivating anaerobic ammonium-oxidizing bacteria that are employed for removing nitrogen from nitrogen containing liquids such as wastewater and anaerobically oxidize ammonium and nitrite, nitrogen components in the nitrogen containing liquids, used as substrates.

2. Description of the Related Art

Nitrogen components contained in nitrogen containing liquids such as sewage and industrial wastewater cause the eutrophication of water systems such as lakes and mashes and cause a reduction in dissolved oxygen in water systems. For these reasons, the nitrogen components must be removed before the nitrogen containing liquids are drained out of the systems. Principal nitrogen components contained in this nitrogen containing liquid are ammonium nitrogen, nitrite nitrogen, nitrate nitrogen, and organic nitrogen.

Conventionally, for treating this kind of wastewater, removal by an ion exchange method and oxidation with chlorine and ozone have been used for wastewater that contains nitrogen at low concentrations, while a method by biological treatment has been adopted for wastewater that contains nitrogen at moderate and high concentrations.

In the biological treatment, nitrification/denitrification treatment by aerobic nitrification and anaerobic denitrification is carried out. In the aerobic nitrification, ammonium nitrogen and nitrite nitrogen in a nitrogen containing liquid to be treated are aerobically oxidized with ammonium-oxidizing bacteria (such as the genera *Nitrosomonas, Nitrosococcus, Nitrosospira,* and *Nitrosolobus*) and nitrite oxidizing bacteria (such as the genera *Nitrobactor, Nitrospira, Nitrococcus,* and *Nitospina*) in a nitrification tank. On the other hand, in the anaerobic denitrification, anaerobic denitrification with heterotrophic bacteria such as *Pseudomonas denitrificans* is performed in a denitrification tank.

In the aerobic nitrification, the nitrification tank is operated at a load ranging from 0.2 to 0.3 kg-N/m³/d. On the other hand, in the anaerobic denitrification, the denitrification tank is operated at a load ranging from 0.2 to 0.4 kg-N/m³/d. Accordingly, when the total nitrogen concentration in the nitrogen containing liquid to be treated falls within the range of 30 to 40 mg/L, a retention time required is 6 to 8 hours for the nitrification tank and 5 to 8 hours for the denitrification tank, leading to a problem that each large-scale treatment tank must be provided.

In addition, the denitrification of nitrogen containing liquids that contain inorganic matter, such as industrial wastewater requires organic matter, although the loads of the nitrification and denitrification tanks are set to the above range. Thus, methanol must be added at a concentration 3 to 4 times greater than a nitrogen concentration in the nitrogen containing liquid to be treated, leading to another problem that large running cost in addition to initial cost is required.

By contrast, nitrogen removal by an anaerobic ammonium oxidation method is recently receiving attention, as disclosed in Japanese Patent Application Laid-Open No. 2001-037467. This anaerobic ammonium oxidation method is a method in which ammonium and nitrite in a nitrogen containing liquid to be treated are used as an electron donor and an electron acceptor, respectively, and are simultaneously denitrified with a group of anaerobic ammonium-oxidizing bacteria according to Chemical Formula 1 (see Strous M. et al., (1998) The sequencing batch reactor as a powerful tool for the study of slowly growing anaerobic ammonium-oxidizing microorganisms. Appl. Microbiol. Biotechnol, 50, 589-596) shown below.

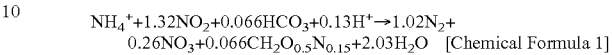
[Chemical Formula 1]

According to the anaerobic ammonium oxidation method, the use of methanol and so on required in conventional denitrification methods can be reduced significantly, because ammonium in the nitrogen containing liquid to be treated is utilized as a hydrogen donor. Additionally, this method also has a merit of reducing the amount of sludge generated by the treatment and as such, is considered to be effective as a future nitrogen removal method.

Microorganisms of the genus *Planctomycetes* have been reported as those responsible for this anaerobic ammonium oxidation reaction (Strous M. et al., (1999) Missing lithotroph identified as new planctomycete. Nature, 400, 446-449).

In general, the growth rates of microorganisms utilized in the above-described nitrogen removal treatment of wastewater are slow, and the yields of their bacterial cells are also low. Thus, the wastewater treatment requires a large amount of bacterial cells of those microorganisms and therefore presents a problem that the cultivation and acclimatization of the microorganisms require a great deal of time.

For dealing with this problem, Japanese Patent Application Laid-Open No. 09-187272 has proposed a method in which a nitrate bacterium with a slow growth rate is efficiently cultivated by controlling the amount of a substrate ammonium added in the logarithmic growth phase of the nitrate bacterium.

The anaerobic ammonium oxidation method is difficult to put to practical use and is not prevalent, in spite of the fact that a large number of anaerobic ammonium oxidation methods have been proposed.

One reason is that the growth rates of anaerobic ammonium-oxidizing bacteria used in the anaerobic ammonium oxidation method are slow, and the yields of the bacterial cells are low. Especially, microorganisms of the genus *Planctomycetes* have been reported to require a doubling time (a time when 1 bacterial cell is grown into 2 bacterial cells) of 11 days. This slow growth is a major challenge to the practical use of the method. Under present circumstances, a method for cultivating these anaerobic ammonium-oxidizing bacteria is not yet reported concretely.

Seed sludge that contains anaerobic ammonium-oxidizing bacteria is required for operating facilities that treat wastewater by the anaerobic ammonium oxidation method. Seed sludge with a large number of bacterial cells must be introduced for starting up a wastewater treatment equipment with stability within a shot time.

However, the efficient cultivation of bacteria requiring a doubling time as long as 11 days as seed sludge is a major challenge to the practical use of wastewater treatment by the anaerobic ammonium oxidation method. The practical use of the anaerobic ammonium oxidation method is in urgent need of overcoming this challenge.

Furthermore, the anaerobic ammonium oxidation method is capable of high-speed treatment as described above. Therefore, the method requires a consumption rate of a substrate as never experienced in cultivating nitrifying bacteria as disclosed in Japanese Patent Application Laid-Open No. 09-187272. In addition, the method requires a long cultivation period because of the slow growth rates of the bacteria and therefore requires an enormous amount of the substrate at the time of cultivation. Thus, the method presents additional problems associated with large cost required for feeding the substrate as well as large cost required for treating a large amount of waste liquids generated by cultivation.

The present invention has been achieved in light of such circumstances, and an object of the present invention is to provide a method and equipment for cultivating anaerobic ammonium-oxidizing bacteria, which can feed substrates without waste to generate seed sludge with high bacterial cell concentrations and can start up operation within a short time, in cultivating anaerobic ammonium-oxidizing bacteria with ammonium and nitrite as substrates.

SUMMARY OF THE INVENTION

For attaining the above-described object according to a first aspect of the present invention, there is provided a method for cultivating anaerobic ammonium-oxidizing bacteria capable of denitrifying ammonium and nitrite substrates, the method comprising: cultivating the bacteria in a cultivation tank; feeding a substrate into the cultivation tank; and controlling a feed rate (Y) of the substrate after the bacteria enters a logarithmic growth phase to satisfy formula: $Y=A\times\exp(K\times T)$, where Y is a feed rate of the substrate, A is a concentration of the substrate at the start of cultivating, K is a feed constant of the substrate, and T is a number of cultivation days after onset of the logarithmic growth phase.

The present inventors have questioned the previously reported doubling time of anaerobic ammonium-oxidizing bacteria and have examined anaerobic ammonium-oxidizing bacteria for a growth rate at a gene level. As a consequence, the present inventors have found that the doubling time is not 11 days, which have previously been reported, but is 1.8 days at most. Based on these novel findings, the present invention provides for the feeding of a substrate without waste to generate seed sludge with high bacterial cell concentrations and the start-up of a cultivation tank by allowing anaerobic ammonium-oxidizing bacteria to glow in the cultivation tank.

As described above, the cultivation tank used in the present invention is not limited to the cultivation of seed sludge of anaerobic ammonium-oxidizing bacteria. When the cultivation tank is an anaerobic ammonium oxidation tank of an actual equipment, the present invention can be applied to the start-up operation of the anaerobic ammonium oxidation tank and can also be applied as a method for acclimatization of anaerobic ammonium-oxidizing bacteria inactivated during operation.

According to the first aspect of the present invention, the feed rate Y of the substrate fed into the cultivation tank is controlled after the anaerobic ammonium-oxidizing bacteria go into a logarithmic growth phase, so as to satisfy the formula: $Y=A\times\exp(K\times T)$. Therefore, the efficient continuous cultivation of the anaerobic ammonium-oxidizing bacteria is made possible, and the anaerobic ammonium-oxidizing bacteria with high concentrations can be prepared easily. It is also possible to eliminate the ineffective feeding of the substrate and thereby conduct efficient cultivation by bringing the feed constant K in agreement with the doubling time obtained as the novel findings, that is, a consumption rate of the substrate by the anaerobic ammonium-oxidizing bacteria. This can feed the substrate without waste to generate seed sludge with high bacterial cell concentrations. Therefore, a reduction in the cost of feeding the substrate as well as a significant reduction in the cost of treating waste liquids can be carried out.

According to a second aspect of the present invention, there is provided the method for cultivating anaerobic ammonium-oxidizing bacteria according to the first aspect, wherein the bacteria are bacteria having a DNA sequence of 16S rRNA gene whose particular region contains at least one sequence included in the group consisting of SEQ ID NO: 1-9.

The gene sequences of the anaerobic ammonium-oxidizing bacteria described in the second aspect are registered in DDBJ (DNA Data Bank of Japan), and the registration numbers are AB164467 for the sequence (1), AB164468 for the sequence (2), AB164469 for the sequence (3), AB164470 for the sequence (4), AB164471 for the sequence (5), AB164472 for the sequence (6), AB164473 for the sequence (7), AB164474 for the sequence (8), and AB164475 for the sequence (9).

In the second aspect, the method of the present invention is applied to bacteria having a DNA sequence of 16S rRNA gene whose particular region contains at least one sequence included in the group consisting of SEQ ID NO: 1-9, and thereby more preferable effect can be obtained.

According to a third aspect of the present invention, there is provided the method for cultivating anaerobic ammonium-oxidizing bacteria according to the first or second aspect, wherein an ammonium substrate and a nitrite substrate are fed into the cultivation tank; and a ratio of ammonium nitrogen to nitrite nitrogen fed into the cultivation tank is controlled in a range of from about 1:0.5 to about 1:2.0.

The third aspect defines the preferable range of the ratio of ammonium nitrogen to nitrite nitrogen, which serve as substrates. The ratio falls within the range of preferably 1:0.5 to 1:2.0, more preferably 1:1 to 1:1.5, particularly preferably 1:1.3.

According to a fourth aspect of the present invention, there is provided the method for cultivating anaerobic ammonium-oxidizing bacteria according to any of the first to third aspects, wherein the feed constant (K) of the substrate is set in the range of 0.05 to 0.28.

The fourth aspect defines the preferable range for setting the feed constant K in agreement with the doubling time obtained as the novel findings. The feed constant K is preferably in the range of 0.05 to 0.28.

If the feed constant K is attempted to be set in agreement with the previously reported doubling time of 11 days, a value of the feed constant K that can be set is 0.069 at the maximum even if the bacterial cell and the growth rate have a 1:1 relationship, that is, an ideal relationship where the treatment rate is doubled as the bacterial cell is doubly increased. Considering that the 1:1 relationship between the bacterial cell and the growth rate never happens in reality, the reasonable value of the feed constant K is less than 0.05. Thus, the value of the feed constant K in the fourth aspect can be set only after the novel findings by the present inventors that the doubling time is 1.8 days are presented.

According to a fifth aspect of the present invention, there is provided the method for cultivating anaerobic ammonium-oxidizing bacteria according to any of the first to third aspects, wherein the feed constant (K) of the substrate is set in the range of 0.06 to 0.15.

The fifth aspect defines the more preferable range of the feed constant K. The feed constant K is more preferably in the range of 0.06 to 0.15. This is because the optimum feed constant K varies somewhat depending on cultivation conditions of the anaerobic ammonium-oxidizing bacteria. Thus, it is preferred that the feed constant K should be set to the range of 0.06 to 0.15 in order to render the feed constant K less susceptible to the cultivation conditions.

According to a sixth aspect of the present invention, there is provided the method for cultivating anaerobic ammonium-oxidizing bacteria according to any of the first to third aspects, wherein the feed constant K of the substrate is set in the range of 0.07 to 0.12.

The sixth aspect defines the range much less susceptible to the cultivation conditions. It is particularly preferred that the feed constant K should be set to this range to cultivate the anaerobic ammonium oxidizing bacteria.

According to a seventh aspect of the present invention, there is provided the method for cultivating anaerobic ammonium-oxidizing bacteria according to any of the first to sixth aspects, further comprising: increasing stepwise the feed rate Y' of the substrate to approach a rising curve represented by the formula: $Y=A \times \exp(K \times T)$; and controlling a nitrite nitrogen concentration in the cultivation tank so that the nitrite nitrogen concentration is 70 mg/L or less.

This is because the anaerobic ammonium-oxidizing bacteria use nitrite as a substrate while they possess unique properties of being decreased in activity or, in extreme cases, being inactivated by exceedingly high nitrite concentrations. Unless cultivation is performed in light of such properties, efficient cultivation cannot be performed.

In the seventh aspect, the substrate is fed into the cultivation tank so that the feed rate Y' of the substrate is increased stepwise to approach a rising curve represented by the formula: $Y=A \times \exp(K \times T)$. Moreover, a nitrite nitrogen concentration increased every single step in the cultivation tank is controlled so as not to exceed 70 mg/L at most. This eliminates a chance that the anaerobic ammonium-oxidizing bacteria are decreased in activity or inactivated during cultivation. It is more preferred to control the nitrite nitrogen concentration increased every single step so as not to exceed 50 mg/L.

According to an eighth aspect of the present invention, there is provided the method for cultivating anaerobic ammonium-oxidizing bacteria according to any of the first to sixth aspects, further comprising, after the anaerobic ammonium-oxidizing bacteria enters the logarithmic growth phase: determining an actual consumption rate (y) of the substrate by comparing a first concentration of the substrate fed into the cultivation tank and a second concentration of the substrate remaining in liquid discharged from the cultivation tank; calculating a consumption constant (k) for the consumption rate of the substrate using formula: $y=a \times \exp(k \times T)$, where y is the actual consumption rate of the substrate, a is a substrate concentration at the start of cultivating, k is the consumption constant of the substrate, T is the number of cultivation days from the onset of the logarithmic growth phase; and setting the feed constant (K) correspond to the calculated consumption constant (k).

The feed constant K is set to the range of 0.05 to 0.28, as described above. In the eighth aspect, the optimum feed constant K in this range is set.

The eighth aspect provides for the further elimination of waste of the substrate and efficient cultivation by setting the feed constant K so that the feed rate of the substrate agrees with the consumption rate of the substrate. Namely, since the actual consumption rate y of the substrate can be determined from a difference between a concentration of the substrate fed into the cultivation tank and a concentration of the substrate remaining in a liquid discharged from the cultivation tank, this determined consumption rate y of the substrate is used to calculate the consumption constant k from the formula $y=a \times \exp(k \times T)$ for the consumption rate of the substrate. Then, the feed constant k can be set to agree with the calculated consumption constant k, thereby using up the substrate fed into the cultivation tank without waste in cultivation.

For attaining the above-described object, according to a ninth aspect of the present invention, there is provided equipment for cultivating anaerobic ammonium-oxidizing bacteria capable of denitrifying ammonium and nitrite substances, the equipment comprising: a cultivation tank for cultivating the bacteria; an ammonium feed device for feeding an ammonium substrate at a given concentration into the cultivation tank; a nitrite feed device for feeding a nitrite substrate at a given concentration into the cultivation tank; and a control device for controlling a feed rate (Y) of each of the substrates after the bacteria enters a logarithmic growth phase to satisfy formula: $Y=A \times \exp(K \times T)$, where Y is a feed rate of the substrate, A is a concentration of the substrate at the start of cultivating, K is a feed constant of the substrate, T is a number of cultivation days after onset of the logarithmic growth phase.

Note that both of "a" and "A" means "a substrate concentration at the start of the cultivation operation". "a" is "a substrate concentration at the start of the cultivation operation" from the point of view of consumption rate, and "A" means "a substrate concentration at the start of the cultivation operation" from the point of view of feed rate.

The ninth aspect provides the present invention constituted as equipment. The control device controls the feed rate Y of the substrate fed into the cultivation tank so as to satisfy the formula: $Y=A \times \exp(K \times T)$, when ammonium and nitrite serving as the substrates are fed from the ammonium feed device and the nitrite feed device into the cultivation tank to cultivate the anaerobic ammonium-oxidizing bacteria. This can feed the substrate without waste to generate seed sludge with high bacterial cell concentrations. Therefore, a reduction in the cost of feeding the substrate as well as a significant reduction in the cost of treating waste liquids can be carried out.

According to a tenth aspect of the present invention, there is provided the equipment for cultivating anaerobic ammonium-oxidizing bacteria according to the ninth aspect, wherein the bacteria are bacteria having a DNA sequence of 16S rRNA gene whose particular region contains at least one sequence included in the group consisting of SEQ ID NO: 1-9.

In the tenth aspect, the equipment of the present invention is applied to bacteria having a DNA sequence of 16S rRNA gene whose particular region contains at least one sequence included in the group consisting of SEQ ID NO: 1-9, and thereby more preferable effect can be obtained.

According to an eleventh aspect of the present invention, there is provided the equipment for cultivating anaerobic ammonium-oxidizing bacteria according to the tenth or eleventh aspect, wherein the control device controls the ammonium feed device and the nitrite feed device so that a ratio of ammonium nitrogen to nitrite nitrogen fed into the cultivation tank is controlled in a range of from about 1:0.5 to about 1:2.0.

The control device controls the ammonium feed device and the nitrite feed device so that the ratio of ammonium nitrogen to nitrite nitrogen fed into the cultivation tank falls within the range of preferably 1:0.5 to 1:2.0, more preferably 1:1 to 1:1.5, particularly preferably 1:1.3.

According to a twelfth aspect of the present invention, there is provided the equipment for cultivating anaerobic ammonium-oxidizing bacteria according to any of the ninth to eleventh aspects, further comprising: a first measurement device for measuring a first concentration of each substrate fed into the cultivation tank; and a second measurement device for measuring a concentration of each substrate remaining in a liquid discharged from the cultivation tank, wherein the control device determines an actual consumption rate (y) of each substrate by comparing the first concentration of the substrate determined by the first measurement device and of the second concentration of the substrate determined by the second measurement device; the control device calculates a consumption constant (k) for the consumption rate of the substrate using formula: y=a×exp(k×T), where y is the actual consumption rate of the substrate, a is a substrate concentration at the start of cultivating, k is the consumption constant of the substrate, T is the number of cultivation days from the onset of the logarithmic growth phase; and the control device sets the feed constant (K) to correspond to the calculated consumption constant (k).

As an example of setting the feed constant K on the basis of the consumption constant k, the feed constant K is set to agree with the consumption constant k. In this way, the further elimination of waste of the substrate and efficient cultivation can be carried out by setting the feed constant K so that the feed rate of the substrate agrees with the consumption rate of the substrate.

As described above, the method and equipment for cultivating anaerobic ammonium-oxidizing bacteria according to the present invention can feed substrates without waste to generate seed sludge with high bacterial cell concentrations and can start up operation within a short time, in cultivating anaerobic ammonium-oxidizing bacteria with ammonium and nitrite as substrates. This allows a reduction in the cost of feeding the substrate as well as a significant reduction in the cost of treating waste liquids.

BRIEF DESCRIPTION OF THE DRAWINGS

FIG. 6 is a diagram for illustrating a relationship between the activity of anaerobic ammonium-oxidizing bacteria and a nitrite nitrogen concentration.

DETAILED DESCRIPTION OF THE PREFERRED EMBODIMENTS

Figure 1:
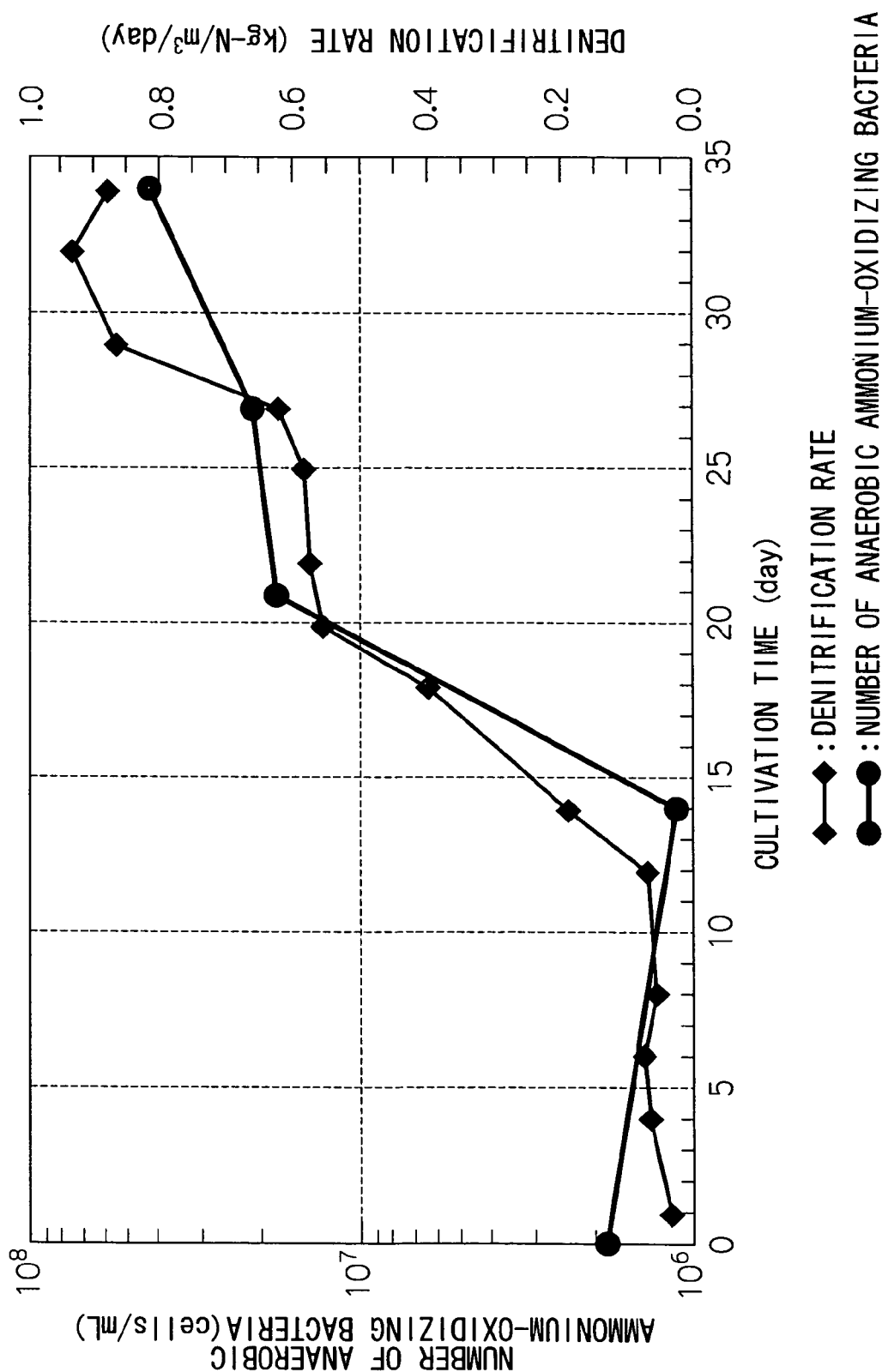
FIG. 1 is a diagram for illustrating a result of a continuous cultivation test conducted for confirming a doubling time of anaerobic ammonium-oxidizing bacteria.

Hereinafter, the preferred embodiments of a method and equipment for cultivating anaerobic ammonium-oxidizing bacteria according to the present invention will be described in detail with reference to the accompanying drawings.

The present inventors have found as described below in accomplishing the present invention.

(1) When anaerobic ammonium-oxidizing bacteria having a DNA sequence of 16S rRNA gene whose particular region contains at least one of the above-described sequences (1) to (9) were examined for a doubling time, the doubling time was not 11 days, which had previously been reported, but was 1.8 days at most. The cultivation of the anaerobic ammonium-oxidizing bacteria having such a doubling time requires a cultivating method based on a technique appropriate thereto. Hereinafter, the anaerobic ammonium-oxidizing bacteria that contain at least one of the above-described sequences (1) to (9) are referred to as "novel anaerobic ammonium-oxidizing bacteria".

(2) The cultivating method comprises controlling a feed rate Y of a substrate fed into a cultivation tank after the novel anaerobic ammonium-oxidizing bacteria go into a logarithmic growth phase, so as to satisfy the following formula: Y=A×exp(K×T) (Calculation Formula 1), wherein the feed rate of the substrate is represented by Y, a feed constant of the substrate is represented by K, the number of cultivation days from the onset of the logarithmic growth phase is represented by T, and a substrate concentration at the start of cultivation operation is represented by A. This allows efficient cultivation without ineffective feeding of the substrate. In this cultivating method, an important thing is that if the substrate concentration is set to A at the start of cultivation operation, cultivation is initiated at this concentration under constant conditions, and the substrate is then given in a larger amount after the novel anaerobic ammonium-oxidizing bacteria go into a logarithmic growth phase, so as to satisfy the Calculation Formula 1. This is because if a large amount of the substrate is introduced into the cultivation tank from the early stage of the cultivation operation before the onset of the logarithmic growth phase, many days are required before the onset of the logarithmic growth phase, and efficient growth is not conducted. The decision as to whether or not the novel anaerobic ammonium-oxidizing bacteria go into the logarithmic growth phase is made according to the point in time when the consumption of the substrate is confirmed. In general, it is preferred that the onset of the logarithmic growth phase should be decided at the point in time when about half the concentration of the substrate fed begins to be consumed. Thus, it is preferred that a cultivating equipment should be provided with a device for detecting the onset of the logarithmic growth phase (which will be described below).

The formula Y=A×exp(K×T) is applied to each of ammonium and nitrite, the substrates of anaerobic ammonium-oxidizing bacteria. The feed rate of the substrate is expressed as Ya=A×exp(K×T) for ammonium. In this case, A means a substrate (ammonium) concentration at the start of cultivation operation, and K means a feed constant of ammonium. Alternatively, the feed rate of the substrate is expressed as Yn=A×exp(K×T) for nitrite, wherein A means a substrate (nitrite) concentration at the start of cultivation operation, and K means a feed constant of nitrite.

(3) The feed constant K of the substrate in the Calculation Formula 1 must be set to a numeric value appropriate to the doubling time of 1.8 days and is set to the range of preferably 0.05 to 0.25, more preferably 0.06 to 0.15, particularly preferably 0.07 to 0.12. For setting this feed constant K more properly, the feed constant K may be set to agree with a consumption constant k determined from a consumption rate of the substrate represented by y=a×exp(k×T) (Calculation Formula 2). In this Calculation Formula 2, the consumption rate of the substrate is represented by y, the number of cultivation days from the onset of the logarithmic growth phase is represented by T, the consumption constant is represented by k, and a substrate concentration at the start of cultivation operation is represented by a.

Next, a cultivation test from which the above-described findings are derived will be described.

(A) A Continuous Cultivation Test for Confirming the Maximum Rate of the Doubling Time (Growth Rate) of the Novel Anaerobic Ammonium-oxidizing Bacteria will be Described First.

A sludge sample used was sludge that contained the novel anaerobic ammonium oxidizing bacteria having all of the above-described sequences (1) to (9) (see Ikuta H, Isaka K, and Sumino T, (2004) Acclimatization of novel anaerobic ammonium-oxidizing bacteria by continuous cultivation system, Proceedings of 38th Annual Meeting of Japan Society on Water Environment, p. 372).

The DNA sequence of 16S rRNA gene of the novel anaerobic ammonium-oxidizing bacteria was confirmed by the following procedures: RNA was extracted therefrom and then amplified with Eub341f primers (Document 1) and AMX 820 primers (Document 2) to confirm the base sequence in a sequencer.

(Document 1) Muyzer G, Brinkhoff T, Nubel U, Santegoeds C, Schafer H, and Wawer C, Denaturing gradient gel electrophoresis (DGGE) in microbial ecology, 1998. 3.4.4, p. 1-27, In Akkermans A. D. L., van Elsas J. D., de Bruijn F. J. (ed.), Molecular microbial ecology manual. Kluwer Academic Publishers, Dordrecht, The Netherlands.

(Document 2) Schmid M, Twachtmann U, Klein M, Strous M, Juretschko S, Jetten M. S. M., Metzger J. W., Schleifer K. H., Wagner M, 2000. Molecular evidence for genus level diversity of bacteria capable of catalyzing anaerobic ammonium oxidation, System. Appl. Microbiol. 23, 93-106.

A wastewater sample used was synthetic inorganic wastewater shown in Table 1. A substrate concentration in the synthetic inorganic wastewater was adjusted by changing ammonium and nitrite concentrations.

TABLE 1

| Substrate | Amount of added | Unit |
| --- | --- | --- |
| NaNO$_2$ | 50~250 (in terms of nitrogen) | mg/L |
| (NH$_4$)SO$_4$ | 50~210 (in terms of nitrogen) | mg/L |
| KHCO$_3$ | 500 | mg/L |
| KH$_2$PO$_4$ | 27 | mg/L |
| MgSO$_4$•7H$_2$O | 300 | mg/L |
| CaCl$_2$•2H$_2$O | 180 | mg/L |
| T. Element S1 | 1 | mL/L |
| T. Element S2 | 1 | mL/L |

Remarks)
T. Element S1: EDTA: 5 g/L, FeSO$_4$: 5 g/L
T. Element S2: EDTA: 15 g/L, ZnSO$_4$•7H$_2$O: 0.43 g/L, CoCl$_2$•6H$_2$O: 0.24 g/L, MnCl$_2$•4H$_2$O: 0.99 g/L, CuSO$_4$•5H$_2$O: 0.25 g/L, NaMoO$_4$•2H$_2$O: 0.22 g/L, NiCl$_2$•6H$_2$O: 0.19 g/L, NaSeO$_4$•10H$_2$O: 0.21 g/L, H$_3$BO$_4$: 0.014 g/L A test equipment used was an upflow cultivation tank (reactor) with an effective volume of 200 mL that was packed with nonwoven cloth made of polyester fiber at a percentage of apparent packing of 50%. A water jacket was placed around the outer circumference of the cultivation tank to adjust water temperature at 37° C.

The sludge that contained the novel anaerobic ammonium-oxidizing bacteria was introduced at an SS concentration of 180 mg/L in the cultivation tank, followed by the continuous cultivation test under conditions of HRT of 3 hours and water temperature of 37° C. A nitrite concentration at the start of cultivation was 70 mg/L in terms of a nitrogen concentration, while an ammonium was set to 80 mg/L in terms of a nitrogen concentration. However, it is desired that ammonium should be introduced in an amount approximately 10 to 20 mg/L larger than the theoretical ratio 1:1.32 of ammonium nitrogen to nitrite nitrogen in an anaerobic ammonium oxidation method, because ammonium might volatilize during the cultivation test to cause a reduction in its concentration, with the result that the nitrite concentration could remain.

The novel anaerobic ammonium-oxidizing bacteria were measured using an FISH (Fluorescence In Situ Hybridization) method, wherein the novel anaerobic ammonium-oxidizing bacteria were stained and then counted under microscopy. The FISH method employs a probe capable of specifically coloring the genes of the anaerobic ammonium-oxidizing bacteria and conducts selective color development. Primers used were AMX820 primers. In this case, the bacteria die during the measurement in the FISH method. Therefore, after being drawn from one cultivation tank and measured, the sludge cannot be returned to the cultivation tank for continuous cultivation. Thus, 4 cultivation tanks placed under the same cultivation conditions were prepared and simultaneously operated. Then, almost all of the bacterial cells in one of the cultivation tanks were washed and collected, followed by measurement, at intervals of one week from the point in time when changes in water quality (denitrification performance) were confirmed (see Schmid M, et al., (2000) Molecular evidence for genus level diversity of bacteria capable of catalyzing anaerobic ammonium oxidation, System. Appl. Microbiol. 23, 93-106).

FIG. 1 is a diagram showing a result of the continuous cultivation test and shows denitrification rates (kg-N/m$_3$/day) of ammonium and nitrite versus a cultivation day, and changes in the number of the anaerobic ammonium-oxidizing bacteria versus a cultivation day.

As shown in FIG. 1, the number (concentration) of the novel anaerobic ammonium-oxidizing bacteria in the cultivation tank was sharply increased from $1.1 \times 10^6$ cells/mL (14th day) to $1.7 \times 10^7$ cells/mL (21st day) for the period likely to be a logarithmic growth phase from the 14th day to the 21st day. It followed gradual growth at $2.1 \times 10^7$ cells/mL on the 27th day and $4.3 \times 10^7$ cells/mL on the 34th day.

Then, the growth rate of the novel anaerobic ammonium-oxidizing bacteria was calculated from the number of the novel anaerobic ammonium-oxidizing bacteria for the period likely to be a logarithmic growth phase from the 14th day to the 21st day. As a result, the doubling time was shown to be 1.8 days, much shorter than the previously reported doubling time of 11 days, and the specific growth rate ($\mu$) was 0.39 days$^{-1}$. The consumption constant of the substrate in the Calculation Formula 2 is allowed to approach $y=0.003 \times \exp(0.28 \times T)$ for the period likely to be a logarithmic growth phase from the 14th day to the 21st day. In this case, the consumption constant k of the substrate is 0.28. Thus, the feed constant K relative to the feed rate Y of the substrate in the Calculation Formula 1 is set to a value on the order of the consumption constant 0.28, thereby allowing efficient cultivation without waste of the substrate.

As can be seen from this result, the growth rate in the logarithmic growth phase from 14th day to 21st day allows the doubling time of 1.8 days at most, in which the novel anaerobic ammonium-oxidizing bacteria can grow at a rate much faster than that in the previously reported doubling time of 11 days.

In this continuous cultivation test, the type and relative number of the novel anaerobic ammonium-oxidizing bacteria were measured by a cloning method (see Document 3) during the early stage of cultivation operation and after the cultivation. As a result, almost no change was observed therein. Namely, the respective novel anaerobic ammonium-oxidizing bacteria having a DNA sequence of 16S rRNA gene whose particular region contains the above-described sequences (1) to (9) were all shown to grow in a similar manner. For further information on the cloning method, see Document 3.

(Document 3) Kaneko N, Yoshie S, Aoi Y, Tuneda S, and Hirata A, (2004) Biological structure analysis of microorganisms involved in anaerobic ammonium oxidation reaction, Proceedings of 38th Annual Meeting of Japan Society on Water Environment, p373.

However, as can bee seen from the result of FIG. 1, the growth rate from the 21st day onward is lower than that from the 14th day to the 21st day. This is because the feed rate of the substrate was not changed, with the result that the feeding of the substrate was more rate-limited than the growth rate of the bacterial cells. Thus, it is quite important to properly control the feed rate of the substrate in consideration of the growth faster than that at the previously reported growth rate. In the present invention, the proper feed rate of the substrate was diligently studied and concretely constituted, which will be described below.

Figure 2:
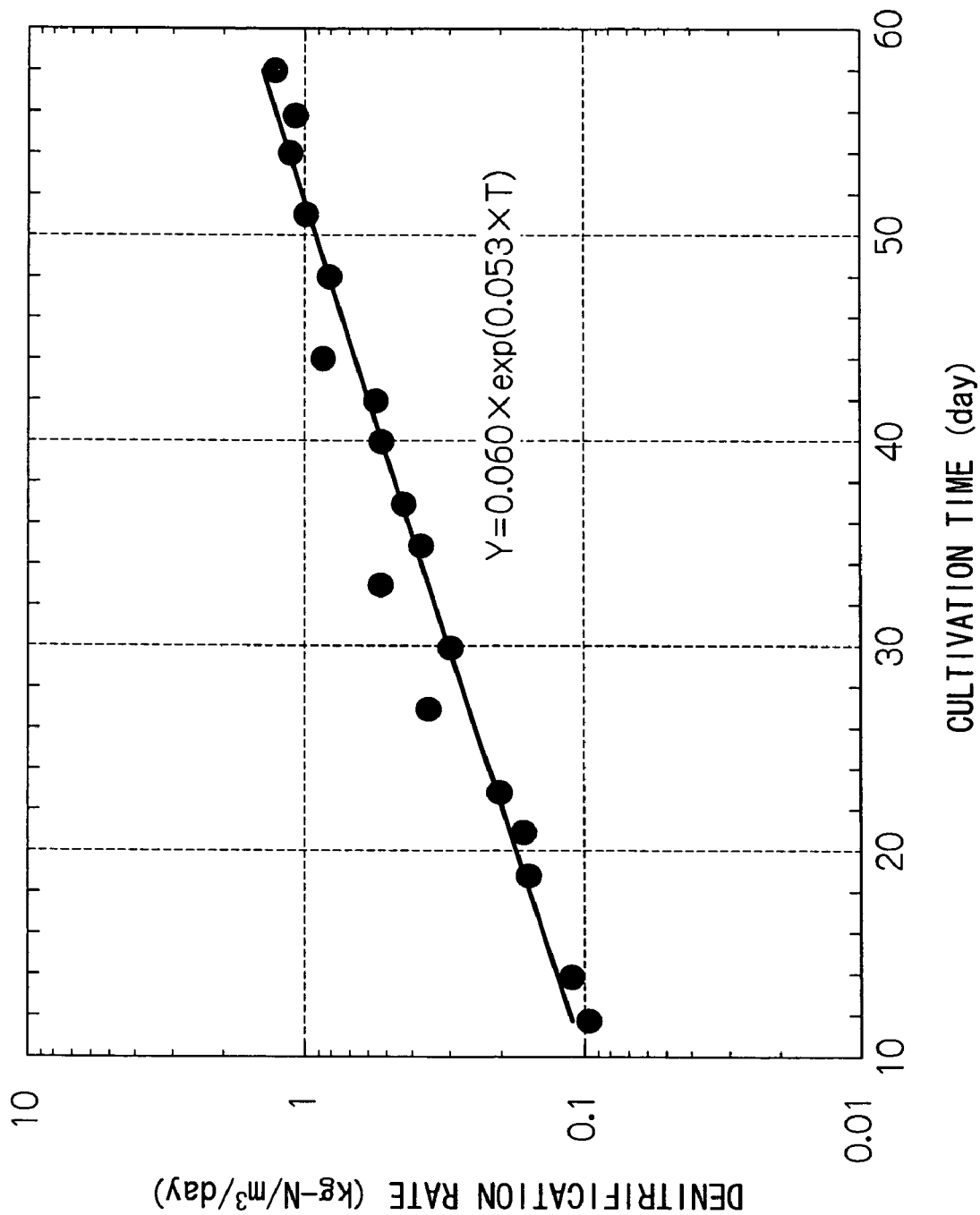
FIG. 2 is a diagram showing a relationship between a cultivation time and a denitrification time when a proper feed rate of a substrate is practiced.

(B) Continuous Cultivation Test Conducted on Proper Feed Rate of Substrate for Cultivating Anaerobic Ammonium-oxidizing Bacteria having Doubling Time of 1.8 Days at Maximum FIG. 2 is a result of a wastewater treatment test conducted without rate-limited feeding of the substrate with use of the novel anaerobic ammonium-oxidizing bacteria entrapped and immobilized, and logarithmically indicates a denitrification rate (kg-N/m$^3$/day) from the 10th day onward when the consumption of the substrate was confirmed, that is, from the logarithmic growth phase onward. As can be seen from in FIG. 2, each plot lays on a straight line, and a cultivation day and the denitrification rate have a close relationship during the logarithmic growth phase over a long time. In this case, the consumption constant k of the substrate was 0.053.

Thus, when there arises the more rate-limited feeding of the substrate than the growth rate of the bacterial cells, which was a problem in the cultivation time from the 21st day onward, it is important, as evident from the drawing, to feed the substrate in agreement with this feed rate of the substrate.

The consumption constant k of the substrate was determined for the logarithmic growth phase (14th day to 21st day) in FIG. 1. As a result, it was k=0.28. Therefore, the test in the paragraph (A) was conducted again by changing a substrate feed procedure. Namely, cultivation was performed from the point in time when the consumption of the substrate was confirmed, so as to satisfy the formula Y=A×exp (K×T) for the feed rate of the substrate. To be more specific, the substrate was fed at a feed rate adjusted to Ya=80×exp(0.28×T) for ammonium and to Yn=70×exp(0.28×T) for nitrite.

As a result, the bacterial cell concentration was 2.7×10$^8$ on the 27th day in the cultivation time. Thus, a continuation of the growth with a fast growth rate maintained was confirmed. Ammonium and nitrite concentrations in the treated water were respectively 40 mg/L or less. It was also confirmed that the substrate concentration in the wastewater after cultivation could be reduced.

(C-1) When Substrate is Introduced in Large Amounts from Early Stage of Cultivation Operation In this test, the same equipment as in the paragraph (A) was used to perform cultivation with a substrate concentration increased in advance. Namely, an ammonium concentration was set to 150 mg/L in terms of a nitrogen concentration, while a nitrite concentration was set to 150 mg/L in terms of a nitrogen concentration. Seed sludge was introduced at an SS concentration of 180 mg/L into the cultivation tank.

As a result, wastewater with each concentration of ammonium and nitrite as high as 140 mg/L in terms of a nitrogen concentration was discharged even for 25 days from the start of cultivation operation, and the number of days required for a logarithmic growth phase to start was as long as 25 days. The consumption constant k relative to the consumption rate y of the substrate was as low as 0.021 even after the onset of the logarithmic growth phase.

(C-2) When Cultivation is Conducted with Feed Constant K Set to 0.09

In this test, the same equipment as in the paragraph (A) was used to perform cultivation. An initial substrate concentration was also the same as in the paragraph (A). The substrates, ammonium and nitrite, were fed at a feed rate adjusted to Ya=80×exp(0.09×T) for ammonium and to Yn=70×exp(0.09×T) for nitrite from the point in time (18th day) when the consumption of the substrate was confirmed.

As a result, from the 14th day to the 27th day in the cultivation time, the novel anaerobic ammonium-oxidizing bacteria could be cultivated at a growth rate that allowed the doubling time of 5 days. Ammonium and nitrite concentrations in the treated water were respectively 5 mg/L or less from the 22nd day onward. As can be seen from this result, the cultivation could be performed at a rate faster than that in the reported doubling time of 11 days, although a slight reduction in the growth rate was caused by the rate-limited feeding of the substrate.

(C-3) Method for Controlling Consumption Rate of Substrate on Basis of Consumption Rate Confirmed—1

In this test, the same equipment as in the paragraph (A) was used to perform cultivation. Seed sludge was introduced at the same concentration (180 mg/L) as in the comparative example. However, as to a substrate feed procedure, ammonium and nitrite concentrations were set to 38 mg/L and 50 mg/L, respectively, in terms of a nitrogen concentration during the early stage of cultivation operation. The cultivation was performed under constant conditions until the consumption of about half the amount of the substrate was confirmed. Monitoring for confirming whether or not about half the amount of the substrate was consumed was performed by providing an inlet and outlet of the cultivation tank with nitrogen measurement devices for ammonium and nitrite.

The consumption of about half the amount of the substrate was confirmed after 9 days into operation, while the consumption constant k relative to the consumption rate y of the substrate in the Calculation Formula 2 exhibited 0.1.

Therefore, the logarithmic growth phase was judged as starting. Then, the feed rate of the substrate was controlled under the condition of the feed constant K=0.1 so as to satisfy the Calculation Formula 1 of the feed rate Y of the substrate. The feed rate Y of the substrate was controlled by changing the substrate concentration with a flow rate of the synthetic inorganic wastewater placed under constant conditions. Specifically, the feed rate of ammonium was set to Ya=38×exp(0.1×T), while the feed rate of nitrite was set to Yn=50×exp(0.1×T).

As a result, a denitrification rate of the cultivation tank could be enhanced to 8.0 kg-N/m$^3$/day within a short time from the start of cultivation operation, and ammonium and nitrite concentrations in the treated water could respectively be reduced to 25 mg/L or less.

As described above, high activity could be obtained, and cultivation could be performed with efficiency. Moreover, it was shown that the amount of the substrate fed could be reduced because of the absence of ineffective feeding of the substrate.

(C-4) Method for Controlling Consumption Rate of Substrate on Basis of Consumption Rate Confirmed—2

In this test, the same equipment as in the paragraph (A) was used to perform cultivation. Seed sludge was introduced at a concentration of 250 mg/L, which was larger than that in the test in the paragraph (C-3). As to a substrate feed procedure, ammonium and nitrite concentrations were set to 50 mg/L and 66 mg/L, respectively, in terms of a nitrogen concentration during the early stage of cultivation operation. The cultivation was performed under constant conditions until the consumption of about half the amount of the substrate was confirmed. Monitoring for confirming whether about half the amount of the substrate was consumed was performed in the same way as in the test in the paragraph (C-3).

The consumption of the substrate started on the 4th day into cultivation operation. Towards the 8th day, the consumption of ammonium and nitrite approached the consumption rate y of the substrate in the Calculation Formula 2, and the consumption constant k=0.14 was obtained.

Therefore, the feed rate Y of the substrate was controlled from the 9th day into cultivation operation so as to satisfy the Calculation Formula 1, while the feed constant K was set to 0.14.

As a result, the substrate was consumed along the feed rate of the substrate in the Calculation Formula 1. The nitrite concentration in the cultivation tank could be maintained constantly at 50 mg/L or less during the logarithmic growth phase. Moreover, no reduction was observed in the activity of the anaerobic ammonium-oxidizing bacteria. This attained high activity within a short time from the start of cultivation operation and efficient cultivation. Moreover, it was also shown that the amount of the substrate fed could be reduced because of the absence of ineffective feeding of the substrate.

These test results show that efficient cultivation can be performed without ineffective feeding of the substrate by performing cultivation before the onset of the logarithmic growth phase at a substrate concentration lower than that after the onset of the logarithmic growth phase under constant conditions and controlling the feed rate Y of the substrate fed into the cultivation tank from the onset of the logarithmic growth phase so as to satisfy $Y=A \times \exp(K \times T)$.

(D) Next, a Continuous Cultivation Test for Setting the Feed Constant K of the Substrate in the Calculation Formula 1 will be Described.

Because anaerobic ammonium-oxidizing bacteria are viable by a system of coexisting microorganisms and are difficult to isolate, the consumption constant k of the substrate varies depending on such conditions as an immobilization method of the novel anaerobic ammonium-oxidizing bacteria, the type of an immobilization material, the shape of the cultivation tank, and the activity of seed sludge. Consequently, the optimum feed constant K also varies somewhat. Thus, for setting a value of the feed constant K, it is necessary to set a value in the range in which its frequency is empirically high.

A cultivation test was performed with the same equipment as in the above-described test for confirming the doubling time by variously changing immobilization methods (entrapment immobilization, adhesion immobilization, and granules using the self-granulation of microorganisms) and immobilization materials for immobilizing the anaerobic ammonium-oxidizing bacteria.

Figure 3:
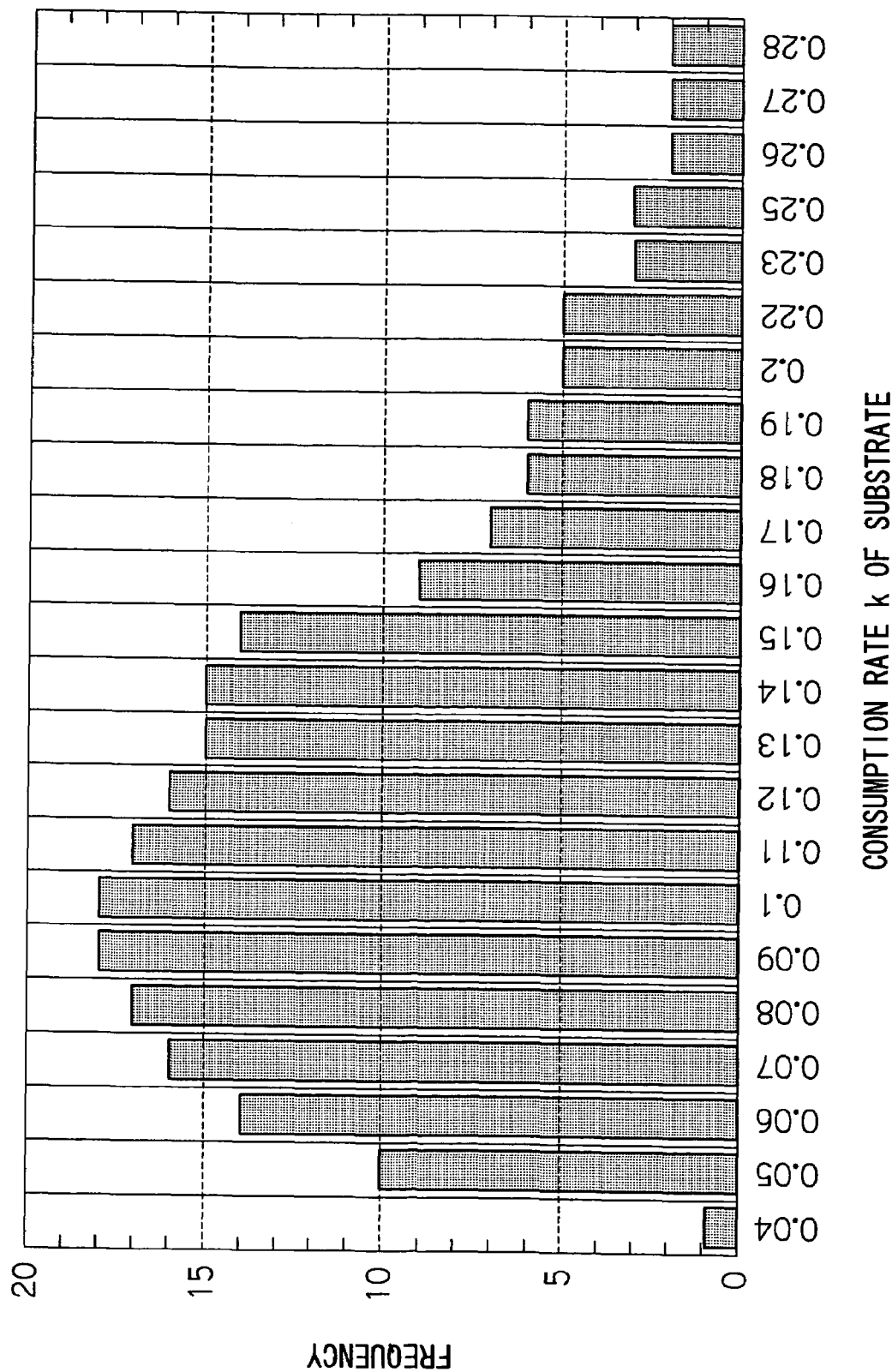
FIG. 3 is a diagram for illustrating a result of a continuous cultivation test conducted for setting a feed constant K in the formula: Y=A×exp(K×T)

As a result, as can be seen from FIG. 3, the value of the consumption constant k of the substrate was observed with a high frequency in the range of 0.05 to 0.28, with a further frequency in the range of 0.06 to 0.15, and with the highest frequency in the range of 0.07 to 0.12, when viewed from the relationship confirmed between the consumption constant k of the substrate and its frequency (frequency of occurrence). Thus, it is preferred that the feed constant K in the Calculation Formula 1 should be set to the range of 0.05 to 0.28 to control the feed rate Y of the substrate. More preferably, the feed constant K falls within the range of 0.06 to 0.15, particularly preferably 0.07 to 0.12. The influence of cultivation conditions can be reduced by setting the feed constant K to these ranges.

In this regard, if the feed constant K is attempted to be set in agreement with the previously reported doubling time of 11 days, a value of the feed constant K that can be set is 0.069 at the maximum even if the bacterial cell and the growth rate have a 1:1 relationship, that is, an ideal relationship where the treatment rate is doubled as the bacterial cell is doubly increased. Considering that the 1:1 relationship between the bacterial cell and the growth rate never happens in reality, the reasonable value of the feed constant K is less than 0.05. Thus, the value of the feed constant K in the above-described ranges can be set only after the novel findings by the present inventors that the doubling time is 1.8 days are presented.

(E) Next, Equipment for Cultivating the Novel Anaerobic Ammonium-oxidizing Bacteria of the Present Invention Constituted on the Basis of the Findings will be Described with Reference to an Overall Block Diagram of thereof.

Figure 4:
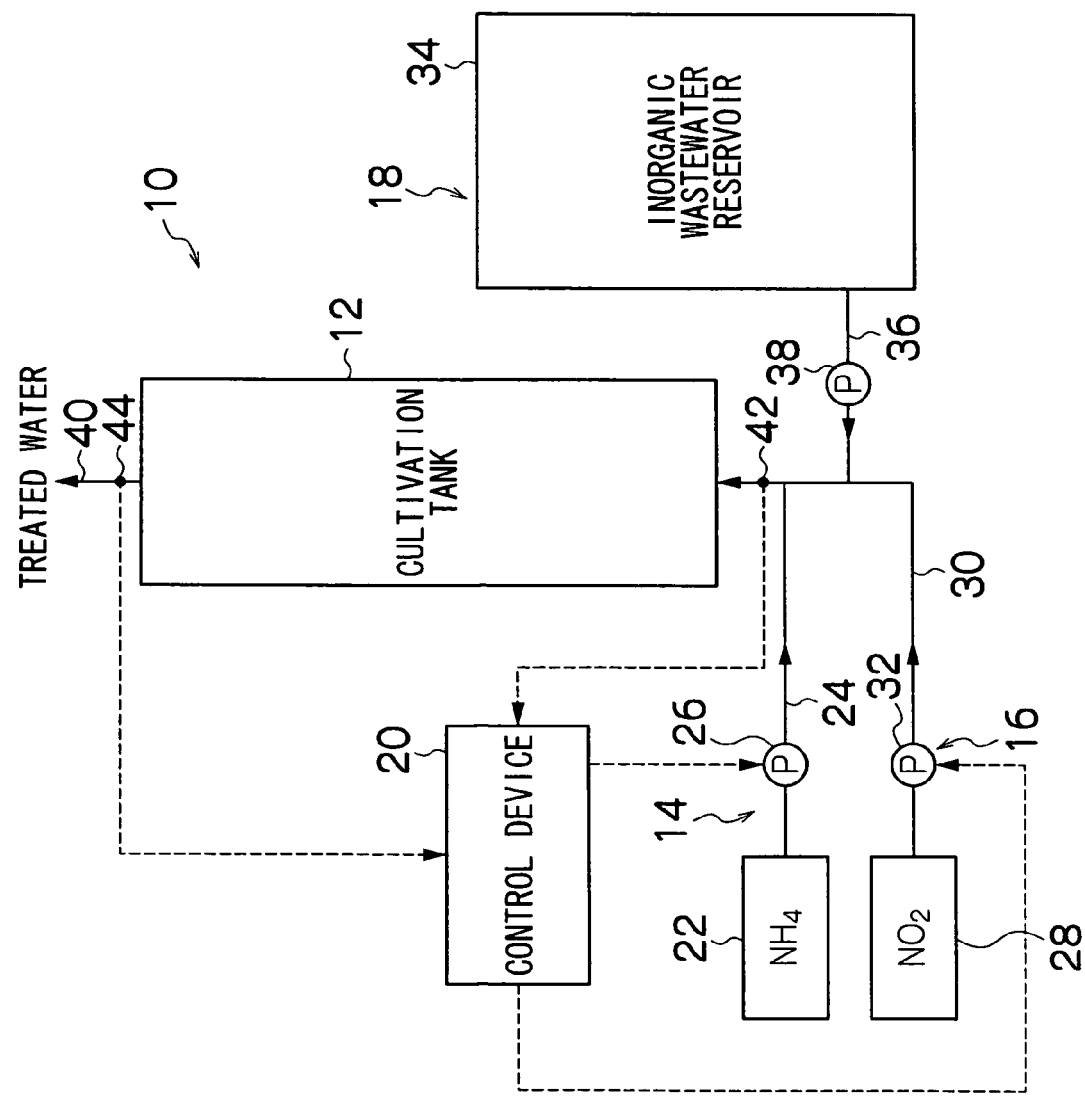
FIG. 4 is an overall block diagram showing equipment for cultivating anaerobic ammonium-oxidizing bacteria of the present invention.

As shown in FIG. 4, equipment 10 for cultivating the novel anaerobic ammonium-oxidizing bacteria is mainly composed of an upflow cultivation tank 12, an ammonium feed device 14 which feeds ammonium (substrate) into the cultivation tank 12, a nitrite feed device 16 which feeds nitrite (substrate) into the cultivation tank 12, a wastewater feed device 18 which feeds wastewater (e.g., synthetic inorganic wastewater) containing the substrate into the cultivation tank 12, and a control device 20 which controls a feed rate of the substrate fed into the cultivation tank 12.

Seed sludge of the anaerobic ammonium-oxidizing bacteria, which has been accumulated and cultivated from, for example, sewage sludge, is introduced into the cultivation tank 12. It is preferred to use fixed beds, adhesion pellets, and entrapment immobilization pellets so that the anaerobic ammonium-oxidizing bacteria do not leak from the cultivation tank 12. Materials that are preferably employed in the fixed beds used include, but not particularly limited to, plastic raw materials such as polyethylene, polyester, polypropylene, and vinyl chloride, and active carbon fiber. The shapes of the fixed beds include, but not particularly limited to, fibrous fixed beds, chrysanthemum-shaped fixed beds, and honeycomb-shaped fixed beds. The apparent volume of the fixed beds is adjusted to preferably 30 to 80%, more preferably 40 to 70%. It is preferred to use fixed beds with a porosity not lower than 80%.

Immobilization materials for the adhesion pellets include, but not particularly limited to, polyvinyl alcohol, alginic acid, polyethylene glycol-based gel, and plastic pellets such as cellulose, polyester, polypropylene, and vinyl chloride. It is preferred to use adhesion pellets shaped into spherical, cylindrical, porous, cubic, sponge-like, or honeycomb-like form, or the like.

Although preferable immobilization materials for the entrapment immobilization pellets are polyethylene glycol-based gel, no particular limitation was imposed on the immobilization materials as long as they have no adverse effect on bacterial cells. In addition to the fixed beds, adhesion pellets, and entrapment immobilization pellets, granules using the self-granulation of microorganisms can also be utilized in the present invention.

In the ammonium feed device 14, a first pipe 24 extends from an ammonium reservoir 22 for retaining an ammonium solution with a given concentration to the bottom of the cultivation tank 12. About the midpoint of the first pipe 24 is provided with a first pump 26 which adjusts the amount of ammonium fed. In the nitrite feed device 16, a second pipe 30 is connected from a nitrite reservoir 28 for retaining a nitrite solution with a given concentration to about the midpoint of the first pipe 24, while about the midpoint of the second pipe 30 is provided with a second pump 32 which adjusts the amount of nitrite fed. It is preferred the ammonium reservoir 22 and the nitrite reservoir 28, which are feed sources of these substrates, should be different tanks in which ammonium and nitrite are retained in a liquid state. However, because nitrite is unstable, it is preferred that nitrite should be homogenized every time it is used, without being maintained in a liquid state for a long time.

In the wastewater feed device, a third pipe 36 is connected from a wastewater reservoir 34 for retaining, for example, synthetic inorganic wastewater, to about the midpoint of the second pipe 30, while about the midpoint of the third pipe 36 is provided with a third pump 38 which adjusts the amount of wastewater fed. These devices allow the addition of the substrates, ammonium and nitrite, and the feeding of wastewater into the bottom of the cultivation tank 12. The novel anaerobic ammonium-oxidizing bacteria are cultivated in the cultivation tank 12. A discharge pipe 40 which discharges, from the cultivation tank 12, wastewater (hereinafter, referred to as the treated water) in which the substrates have been consumed is connected to the upper end of the cultivation tank 12.

An inlet (first pipe 24 in FIG. 4) of the cultivation tank 12 is provided with a first nitrogen measurement device 42 which detects nitrogen concentrations of ammonium and nitrite fed into the cultivation tank 12, while an outlet (discharge pipe 40 in FIG. 4) of the cultivation tank 12 is provided with a second nitrogen measurement device 44 which measures nitrogen concentrations of ammonium and nitrite remaining in the treated water discharged from the cultivation tank 12. Measurement values determined in the first and second nitrogen measurement devices 42 and 44 are sequentially input into the control device 20.

The control device 20 is installed in advance with Calculation Formula 1 of a feed rate Y of the substrate represented by $Y = A \times \exp(K \times T)$ and Calculation Formula 2 of a consumption rate y of the substrate represented by $y = a \times \exp(k \times T)$. In these formulas, Y represents the feed rate of the substrate, K represents a feed constant of the substrate, T represents the number of cultivation days from the onset of a logarithmic growth phase, A represents a substrate concentration at the start of cultivation operation, y represents the consumption rate of the substrate, k represents a consumption constant of the substrate, and a represents a substrate concentration at the start of cultivation operation. The control device 20 controls the feed rate Y of the substrate fed into the cultivation tank 12 according to Calculation Formula 1. The control device 20 determines an actual consumption rate y of the substrate from a difference between a measurement value of the first nitrogen measurement device 42 and a measurement value of the second nitrogen measurement device 44, that is, from the amount of the substrate consumed by cultivation, then calculates the consumption constant k of the substrate from the determined consumption rate y of the substrate and Calculation Formula 2, and sets the feed constant K for Calculation Formula 1 on the basis of the calculated consumption constant k. For example, the feed constant K is set to agree with the consumption constant k. By this procedure, a value of the feed constant K can be pinpointed and optimally set from within the range of 0.05 to 0.28.

For cultivating the novel anaerobic ammonium-oxidizing bacteria with the cultivating equipment 10 constituted as described above, the control device 20 sets the substrate concentration to A for each of ammonium and nitrite at the start of cultivation operation and initiates cultivation at this concentration under constant conditions. After the novel anaerobic ammonium-oxidizing bacteria go into a logarithmic growth phase, the control device 20 controls the feed rate Y of the substrate fed into the cultivation tank 12, so as to satisfy Calculation Formula 1 $Y = A \times \exp(K \times T)$. In this case, the ratio of ammonium nitrogen to nitrite nitrogen fed into the cultivation tank 12 is in the range of preferably 1:0.5 to 1:2.0, more preferably 1:1 to 1:1.5, particularly preferably 1:1.3.

In such cultivation, whether or not the novel anaerobic ammonium-oxidizing bacteria go into the logarithmic growth phase can be known by the first and second nitrogen measurement devices 42 and 44. Namely, when the consumption of the substrate is sharply increased after the onset of the logarithmic growth phase, a difference between a measurement value of the first nitrogen measurement device 42 and a measurement value of the second nitrogen measurement device 44 is rapidly changed to be small. Thus, the onset of the logarithmic growth phase can be ascertained by monitoring this change. For example, when the measurement value of the second nitrogen measurement device 44 becomes half the measurement value of the first nitrogen measurement device 42, the logarithmic growth phase can be regarded as starting.

The equipment 10 for cultivating the novel anaerobic ammonium-oxidizing bacteria of the present invention constituted as described above is equipment which efficiently cultivates anaerobic ammonium-oxidizing bacteria and is not intended to be limited to the acquisition of seed sludge. For example, when the cultivation tank is regarded as an anaerobic ammonium oxidation tank of a wastewater treatment equipment, the equipment 10 can also be utilized as an acclimatization method at the start of equipment operation or at the time of occurrence of inactivation of anaerobic ammonium-oxidizing bacteria in the anaerobic ammonium oxidation tank.

When the novel anaerobic ammonium-oxidizing bacteria cultivated in the cultivation tank 12 are added to an anaerobic ammonium-oxidizing bacteria tank in a wastewater treatment equipment, it is preferred that the novel anaerobic ammonium-oxidizing bacteria should be entrapped and immobilized for use. Next, the cultivation of the novel anaerobic ammonium-oxidizing bacteria in entrapment immobilization pellets will be described.

The cultivating equipment 10 shown in FIG. 4 was used in this pellet cultivation test, wherein the novel anaerobic ammonium-oxidizing bacteria were entrapped and immobilized in pellet gel and then added into the cultivation tank 12, followed by cultivation. The immobilization gel used was a polyethylene glycol-based prepolymer with a polymer concentration adjusted to 15%. The anaerobic ammonium-oxidizing bacteria were entrapped and immobilized at an SS concentration of 3000 mg/L into this immobilization gel. Then, this entrapment immobilization pellet was packed at a percentage of pellet packing of 10% into the cultivation tank 12.

Wastewater used in the test was synthetic inorganic wastewater shown in Table 1. Ammonium and nitrite concentrations at the start of operation were respectively set to 50 mg/L in terms of a nitrogen concentration. Then, the substrates were fed into the cultivation tank 12 so as to satisfy Calculation Formula 1 with water quality measured, while the concentration of nitrite remaining in the treated water discharged from the cultivation tank 12 was controlled so as not to exceed 50 mg/L in terms of a nitrogen concentration.

Figure 5:
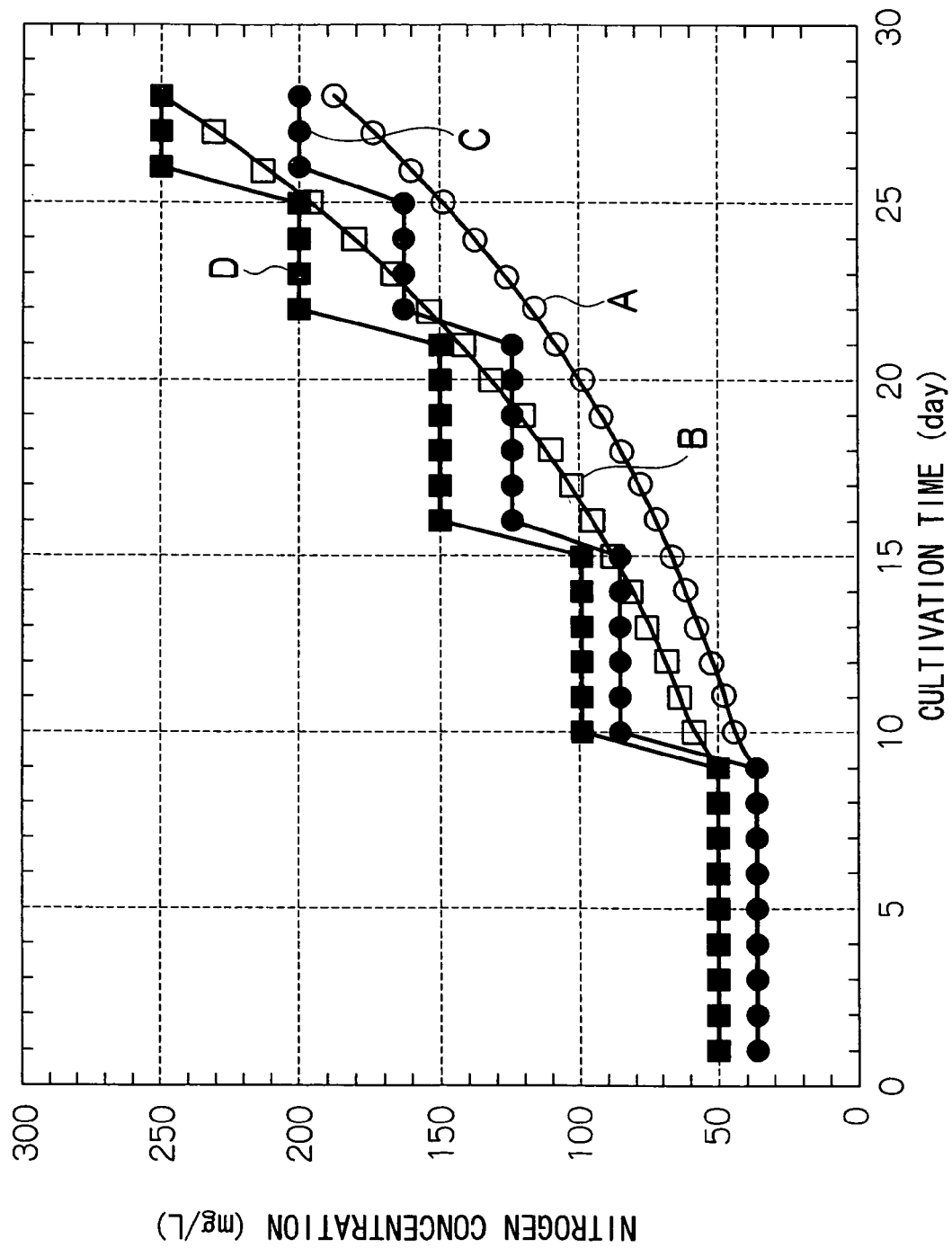
FIG. 5 is a diagram for illustrating a stepwise feed procedure as one aspect of substrate feed procedures.

FIG. 5 shows a modification (stepwise feed procedure) of a feed and control procedure for the substrate fed into the cultivation tank by use of the cultivating equipment 10 shown in FIG. 4. Namely, the stepwise feed procedure increases stepwise the feed rate Y of the substrate to approach a rising curve represented by Calculation Formula 1 and controls a nitrite nitrogen concentration increased every single step in the cultivation tank so as not to exceed 70 mg/L at most. In this test, the nitrite concentration is controlled so as not to exceed 50 mg/L in terms of a nitrogen concentration.

Wastewater used was synthetic inorganic wastewater shown in Table 1. Seed sludge was introduced at a concentration of 220 mg/L into the cultivation tank 12. Ammonium and nitrite concentrations during the early stage of cultivation operation were set to 38 mg/L and 50 mg/L, respectively, in terms of a nitrogen concentration. The cultivation was performed under constant conditions until the consumption of the nitrite nitrogen concentration to 10 mg/L was confirmed. Thereafter, the logarithmic growth phase was judged as starting, and the feeding of the substrate was controlled so as to satisfy Calculation Formula 1.

In the control of feeding of the substrate, a rising curve A indicated by ○ is derived from the case in which the feed rate of ammonium is controlled so as to satisfy Calculation Formula 1, and a rising curve B indicated by □ is derived from the case in which the feed rate of nitrite is controlled so as to satisfy Calculation Formula 1, as shown in FIG. 5. By contrast, a stepwise line C indicated by ● is derived from the case in which the feed rate of ammonium is increased stepwise to approach the rising curve A represented by Calculation Formula 1, and a stepwise line D indicated by ■ is derived from the case in which the feed rate of nitrite is increased stepwise to approach the rising curve B represented by Calculation Formula 1.

As a result, the nitrite nitrogen concentration was decreased to 8 mg/L in measurement on the 9th day. In this case, the consumption constant k of the rising curve B determined from Calculation Formula 2 was 0.08.

A concentration at which nitrite is fed may be changed in agreement with the rising curve B. In the stepwise feeding in this test, cultivation was performed while the nitrite nitrogen concentration in the cultivation tank 12 was increased on the basis of the rising curve B with 50 mg/L aliquots at intervals of approximately five days when the cultivation tank 12 got short of nitrite. Ammonium was fed in an amount based on the nitrite nitrogen concentration so as to attain the ammonium nitrogen concentration equal to or more than a value determined by dividing the nitrite nitrogen concentration by 1.32. As a result, the anaerobic ammonium-oxidizing bacteria could be cultivated at a high consumption constant k kept at 0.08, while maintaining high activity.

As described above, the anaerobic ammonium-oxidizing bacteria use nitrite as a substrate. On the other hand, they are decreased in activity or inactivated by exceedingly high nitrite concentrations. Therefore, when the anaerobic ammonium-oxidizing bacteria are cultivated with the substrate fed stepwise, it is important to use caution not to sharply increase the nitrite nitrogen concentration in the cultivation tank 12. This is also obvious from FIG. 6 showing a relationship between a nitrogen concentration of nitrite remaining in the cultivation tank 12 and the activity of anaerobic ammonium-oxidizing bacteria.

FIG. 6 shows a relationship between a nitrogen concentration of nitrite remaining in the cultivation tank 12 and the activity of anaerobic ammonium-oxidizing bacteria after the nitrite nitrogen concentration in the cultivation tank 12 is sharply increased.

As can be seen from FIG. 6, the activity is 100 when the nitrogen concentration of nitrite remaining in the cultivation tank 12 is 50 mg/L or less. However, the activity is reduced gradually after the nitrite nitrogen concentration exceeds 50 mg/L, and sharply after the nitrite nitrogen concentration exceeds 70 mg/L. Thus, when the substrate is fed and increased stepwise in the cultivation tank 12, it is preferred to control the nitrite nitrogen concentration increased every single step in the cultivation tank 12 so as not to exceed 70 mg/L at most, and it is more preferred to control it at 50 mg/L or less.

The feed rate of the substrate may be adjusted by a method that adjusts the concentration of the substrate or adjusts the flow rate of feeding of the substrate.

What is claimed is:

1. A method for cultivating anaerobic ammonium-oxidizing bacteria capable of denitrifying ammonium and nitrite substrates, the method comprising:
   cultivating the bacteria in a cultivation tank;
   feeding a substrate into the cultivation tank; and
   controlling a feed rate (Y) of the substrate after the bacteria enters a logarithmic growth phase to satisfy formula (I):

$$Y = A \times \exp(K \times T) \qquad \text{(I)}$$

where Y is a feed rate of the substrate, A is a concentration of the substrate at the start of cultivation, K is a feed constant of the substrate, and T is a number of cultivation days after onset of the logarithmic growth phase.

2. The method of claim 1, wherein:
   the bacteria are bacteria having a DNA sequence of 16S rRNA gene whose particular region contains at least one sequence included in the group consisting of SEQ ID NO: 1-9.

3. The method of claim 1 or 2, wherein:
   an ammonium substrate and a nitrite substrate are fed into the cultivation tank; and
   a ratio of ammonium nitrogen to nitrite nitrogen fed into the cultivation tank is controlled in a range of from about 1:0.5 to about 1:2.0.

4. The method of claim 1 or 2, wherein the feed constant (K) of the substrate is set in a range of from about 0.05 to about 0.28.

5. The method of claim 3, wherein the feed constant (K) of the substrate is set in a range of from about 0.05 to about 0.28.

6. The method of claim 1 or 2, wherein the feed constant (K) of the substrate is set in a range of from about 0.06 to about 0.15.

7. The method of claim 3, wherein the feed constant (K) of the substrate is set in a range of from about 0.06 to about 0.15.

8. The method of claim 1 or 2, wherein the feed constant (K) of the substrate is set in a range of from about 0.07 to about 0.12.

9. The method of claim 3, wherein the feed constant (K) of the substrate is set in a range of from about 0.07 to about 0.12.

10. The method of claim 1 or 2, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

11. The method of claim 3, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

12. The method of claim 4 further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

13. The method of claim 5, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

14. The method of claim 6, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

15. The method of claim 7, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

16. The method of claim 8, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

17. The method of claim 9, further comprising:
    increasing stepwise the feed rate (Y') of the substrate to approach a rising curve represented by formula (I); and
    controlling a nitrite nitrogen concentration in the cultivation tank so that the nitrite nitrogen concentration is 70 mg/L or less.

18. The method of claim 1 or 2, further comprising, after the bacteria enters the logarithmic growth phase:
    determining an actual consumption rate (y) of the substrate by comparing a first concentration of the substrate fed into the cultivation tank and a second concentration of the substrate remaining in liquid discharged from the cultivation tank;
    calculating a consumption constant (k) for the consumption rate of the substrate using formula (II):

$$y = a \times \exp(k \times T) \qquad \text{(II)}$$

where y is the actual consumption rate of the substrate, a is a substrate concentration at the start of cultivating, k is the consumption constant of the substrate, T is the number of cultivation days from the onset of the logarithmic growth phase; and
    setting the feed constant (K) to correspond to the calculated consumption constant (k).

19. The method of claim 3, further comprising, after the bacteria enters the logarithmic growth phase:
    determining an actual consumption rate (y) of the substrate by comparing a first concentration of the substrate fed into the cultivation tank and a second concentration of the substrate remaining in liquid discharged from the cultivation tank;
    calculating a consumption constant (k) for the consumption rate of the substrate using formula (II):

$$y = a \times \exp(k \times T) \qquad \text{(II)}$$

where y is the actual consumption rate of the substrate, a is a substrate concentration at the start of cultivating, k is the consumption constant of the substrate, T is the number of cultivation days from the onset of the logarithmic growth phase; and
    setting the feed constant (K) to correspond to the calculated consumption constant (k).

20. The method of claim 4, further comprising, after the bacteria enters the logarithmic growth phase:
    determining an actual consumption rate (y) of the substrate by comparing a first concentration of the substrate fed into the cultivation tank and a second concentration of the substrate remaining in liquid discharged from the cultivation tank;
    calculating a consumption constant (k) for the consumption rate of the substrate using formula (II):

$$y = a \times \exp(k \times T) \qquad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

21. The method of claim 5, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

22. The method of claim 6, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

23. The method of claim 7, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

24. The method of claim 8, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

25. The method of claim 9, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

26. The method of claim 10, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

27. The method of claim 11, further comprising, after the bacteria enters the logarithmic growth phase:

determining an actual consumption rate (y) of the substrate by comparing a first concentration of the substrate fed into the cultivation tank and a second concentration of the substrate remaining in liquid discharged from the cultivation tank;

calculating a consumption constant (k) for the consumption rate of the substrate using formula (II):

$$y = a \times \exp(k \times T) \quad \text{(II)}$$

where y is the actual consumption rate of the substrate, a is a substrate concentration at the start of cultivating, k is the consumption constant of the substrate, T is the number of cultivation days from the onset of the logarithmic growth phase; and setting the feed constant (K) to correspond to the calculated consumption constant (k).

28. The method of claim 12, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

29. The method of claim 13, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

30. The method of claim 14, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

31. The method of claim 15, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

32. The method of claim 16, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

33. The method of claim 17, further comprising, after the bacteria enters the logarithmic growth phase:
- determining an actual consumption rate (y) of the substrate by comparing a first concentration of the substrate fed into the cultivation tank and a second concentration of the substrate remaining in liquid discharged from the cultivation tank;
- calculating a consumption constant (k) for the consumption rate of the substrate using formula (II):

$$y = a \times \exp(k \times T) \tag{II}$$

where y is the actual consumption rate of the substrate, a is a substrate concentration at the start of cultivating, k is the consumption constant of the substrate, T is the number of cultivation days from the onset of the logarithmic growth phase; and
- setting the feed constant (K) to correspond to the calculated consumption constant (k).

* * * * *